United States Patent [19]

Renger

[11] Patent Number: 5,598,847
[45] Date of Patent: Feb. 4, 1997

[54] IMPLANTABLE FLOW SENSOR APPARATUS AND METHOD

[75] Inventor: Herman L. Renger, Calabasas, Calif.

[73] Assignee: Pacesetter, Inc., Sylmar, Calif.

[21] Appl. No.: 365,265

[22] Filed: Dec. 28, 1994

[51] Int. Cl.⁶ ........................................ A61B 5/00
[52] U.S. Cl. ..................... 128/691; 128/692; 128/713; 128/736; 73/204.11; 73/861
[58] Field of Search .................... 128/691, 692, 128/698, 713, 736; 73/204.11, 204.13, 204.23, 861

[56] References Cited

U.S. PATENT DOCUMENTS

| 3,196,679 | 7/1965 | Howland | 703/204.11 |
| 4,555,940 | 12/1985 | Renger | 73/204 |
| 5,040,422 | 8/1991 | Frankenberger et al. | 128/692 |
| 5,230,245 | 7/1993 | Kamiunten et al. | 703/204.11 |
| 5,357,967 | 10/1994 | Dixon et al. | 128/691 |

*Primary Examiner*—Angela D. Sykes
*Assistant Examiner*—Robert L. Nasser, Jr.
*Attorney, Agent, or Firm*—Harold C. Schloss

[57] ABSTRACT

An implantable blood flow sensor for measuring a blood flow rate through a blood vessel within a person's body. The flow sensor includes a rigid cylindrical tube, sized to fit within the blood vessel, a heater attached to the tube, and a pyroelectric detector located within the tube. A predetermined amount of heat energy is produced by the heater and the pyroelectric detector monitors the resultant temperature change and generates a temperature signal based on the temperature change. A processor generates a data signal, based on the temperature change, that indicates the blood flow rate through the blood vessel or artery. The rigid tube protects the pyroelectric detector from external forces that may produce unwanted signals due to piezoelectric effects. Additionally, the heater may be incorporated into one of the electrodes of the pyroelectric detector as a serpentine path in the electrode that forms a resistive heating element. Also, a switch may be provided that prevents induced voltage signals caused by currents through the heater from reaching the processor.

14 Claims, 5 Drawing Sheets

FIG. 5
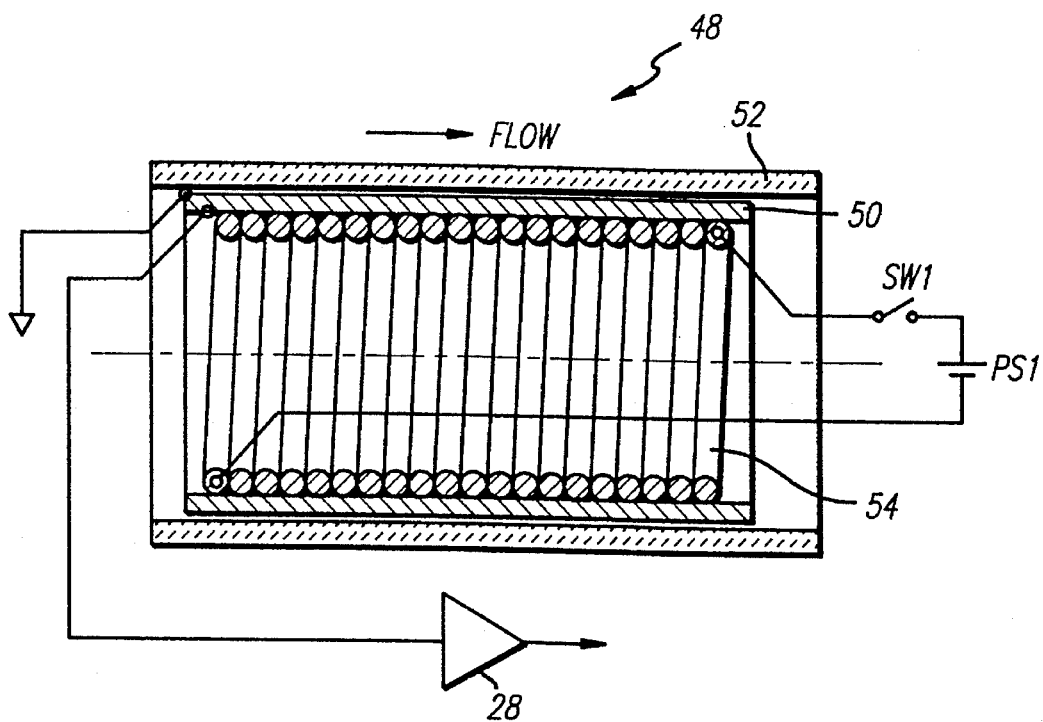
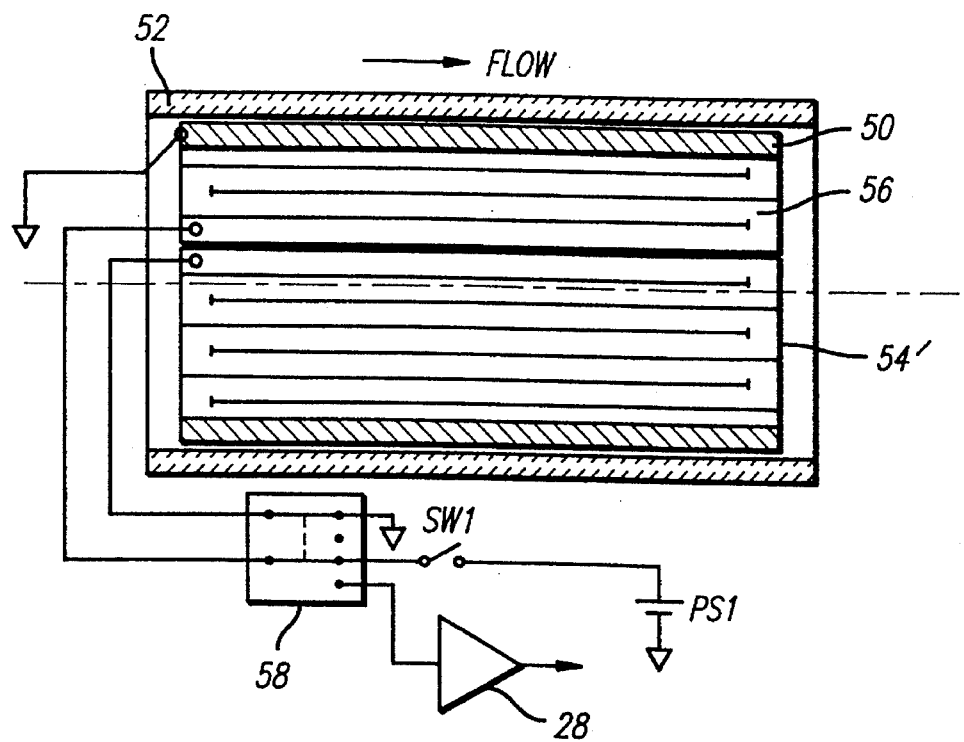
FIG. 6

IMPLANTABLE FLOW SENSOR APPARATUS AND METHOD

BACKGROUND OF THE INVENTION

This invention relates generally to flow sensors for monitoring the volume and rate of fluid flow through a fluid flow path and, more particularly, to miniature flow sensors configured to be implanted in a human body for measurement of blood flow within the circulatory system.

It has been known in the past that fluid flow through a tubular flow path can be measured using an electrical heater and a pyroelectric detector that are mounted on the outside of the flow path. The heater heats the fluid and the pyroelectric detector detects the resulting temperature change as the fluid flows through the fluid path. However, in many cases, such flow sensors cannot sense the direction of fluid flow and can erroneously consider a negative fluid flow to be a positive fluid flow.

Flow sensors may be incorporated into an implantable medical device such as a cardiac pacemaker by sizing the sensors to have a sufficiently small diameter. However, the small size of these sensors requires the heater and the detector, and their associated electrical conductors, to be in close proximity. Conductors in close proximity tend to induce unwanted signals upon each other that may interfere with the proper monitoring of the fluid flow. The proper operation of certain critical medical devices, such as cardiac pacemakers, renders unacceptable flow sensors that can generate unwanted or stray electrical signals.

Accordingly, there exists a need for an implantable flow sensor and related readout circuitry that is sensitive over a wide range of fluid flow rates and that does not produce unwanted or stray electrical signals when implanted in the body. There also exists a need for an implantable flow sensor that provides an indication of the fluid flow direction. The present invention satisfies these needs.

SUMMARY OF THE INVENTION

The present invention provides an implantable fluid flow sensor that includes a rigid tube, a heater, and one or more pyroelectric detectors, for measuring the fluid flow rate within a fluid path. The flow sensor is relatively insensitive to external forces that would cause unwanted electrical signals. Also, if provided with more than one pyroelectric detector, the flow sensor can determine the direction of the fluid flow.

More particularly, the implantable flow sensor includes a rigid tube sized to fit within the fluid path, an electrical heater located within the tube for producing a predetermined amount of heat energy to increase the temperature of the fluid within the fluid path, and a first pyroelectric detector also located within the tube for detecting changes in temperature caused by the heat energy and for generating a temperature signal based on the detected temperature change. The flow sensor also includes a processor that generates a data signal based on the temperature signal. The data signal indicates the fluid flow rate within the fluid path by appropriately processing the temperature signal. The flow sensor has particular utility when integrated with a catheter of an implantable cardiac pacemaker, for measuring blood flow rate.

In a more detailed feature of the invention, the first pyroelectric detector has first and second electrodes spaced apart from each other by a pyroelectric material, and the first electrode can be resistive and can constitute the heater. For example, the first electrode may be a conductor etched in a serpentine path on the surface of the first pyroelectric detector to form the heater.

Additionally, the rigid tube may have a rigid cylindrical shape and the pyroelectric detector may be a cylinder coaxially mounted within the tube, for isolation from external forces applied to the tube. Also, the implantable flow sensor may further include a second pyroelectric detector that operates in conjunction with the first pyroelectric detector, to measure the direction of fluid flow.

In another embodiment of the invention, the implantable flow sensor includes a rigid tube sized to fit within the fluid path and to allow the fluid to flow around the tube and further includes a pyroelectric detector formed of a relatively thin sheet of pyroelectric material attached to either surface of the tube. The pyroelectric detector detects changes in temperature and generates a temperature signal based on the temperature change. The pyroelectric detector has a first detector electrode sandwiched between the tube surface and one surface of the pyroelectric material and a second detector electrode etched in a serpentine path on the other surface of the pyroelectric detector, to form a heater. The flow sensor also includes an electrical power source that is switchably connected to the heater for a predetermined time period, to cause the heater to produce a predetermined amount of heat energy, and an amplifier having an input terminal that receives the temperature signal from the pyroelectric detector. The amplifier buffers the received temperature signal and produces a data signal that indicates the fluid flow rate within the fluid path. A switch is connected to the input terminal of the amplifier and is configured to operate during the predetermined time period so that stray signals produced by currents through the heater are not amplified.

Other features and advantages of the present invention should become apparent from the following description of the preferred embodiments, taken in conjunction with the accompanying drawings, which illustrate, by way of example, the principles of the invention.

BRIEF DESCRIPTION OF THE DRAWINGS

FIG. 5 is a cross-sectional view of a fourth embodiment of an implantable flow sensor of the present invention, having a radially acting heater element, with a schematic depiction of its associated control and monitoring circuitry.

FIG. 6 is a cross-sectional view of a fifth embodiment of an implantable flow sensor of the present invention, having an integral radially acting heater element, with a schematic depiction of its associated control and monitoring circuity.

DESCRIPTION OF THE PREFERRED EMBODIMENTS

Figure 1:
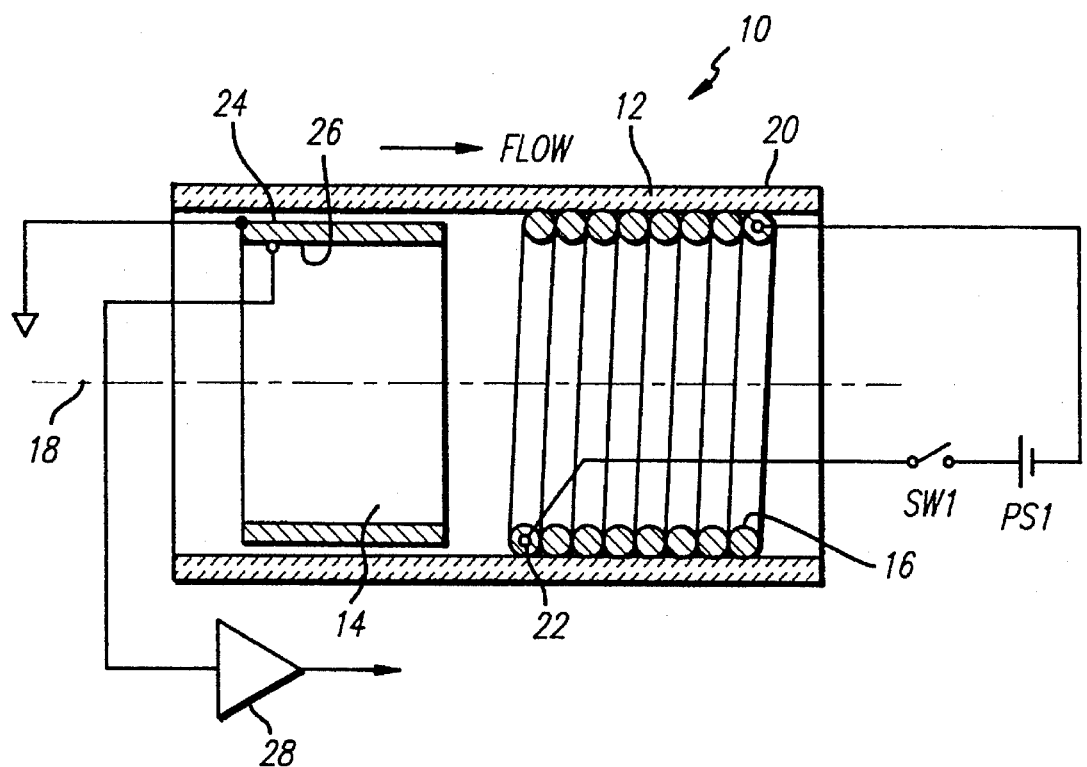
FIG. 1 is a cross-sectional view of a first embodiment of an implantable flow sensor of the present invention, with a schematic depiction of its associated control and monitoring circuitry.

As shown in the exemplary drawings, and particularly in FIG. 1, the present invention is embodied in an implantable flow sensor apparatus, and related method, generally referred to by the reference numeral 10, for measuring fluid flow within a body vessel. In all of the disclosed embodiments, the flow sensor includes a tube, a heater, and a temperature detector that provide a signal indicative of the axial flow rate in the vicinity of the sensor. The small, rugged design of this flow sensor improves its operation under a variety of conditions, such as when implanted within the body.

As shown in FIG. 1, an embodiment of the implantable flow sensor 10 in accordance with the present invention is shown to include a tube 12 encircling a pyroelectric detector 14 and a heater 16. The tube protects the pyroelectric detector from compression or mechanical damage.

The heater 16 is a coil of resistance wire having its axis coaxially aligned with the axis 18 of the tube 12. The outside surface of the heater coil is secured to the inside surface of the tube by an appropriate glue or the like. The electrical circuit for operating the heater includes a power source, such as a battery PS1, and a switch SW1, connected in series between the heater's terminals 20 and 22.

The pyroelectric detector 14 preferably is a cylinder of pyroelectric material, such as a relatively thin sheet of polyvinylidene fluoride (e.g., Kynar), having two electrically isolated electrodes 24 and 26. One electrode 24 is located on the cylinder's outside surface, and the other electrode 26 is located on the cylinder's inside surface. The electrodes are preferably formed of evaporated aluminum or, alternatively, lightly baked conductive ink. The detector also is secured to the inside surface of the tube 12 by an appropriate glue or the like. Alternatively, the outside electrode 24 of the detector can be formed on the inside surface of the tube, and the pyroelectric material attached directly to the tube.

The pyroelectric detector 14 produces about 5 to 20 microcoulombs per square meter of surface area per degree Kelvin. The output voltage signal produced by the detector is based on the change in temperature of the detector. An amplifier 28 buffers and otherwise processes the output voltage signal to produce an electrical signal indicating the flow rate through the sensor. The pyroelectric detector is sufficiently sensitive that a determination of the flow rate can be made with as little as 5 microjoules of heat energy per sample. Such low energy requirements are especially useful in medical devices that are implanted in the body, in which battery power is strictly limited and thermal injury must be avoided.

Preferably, the detector 14 is located upstream of the heater 16, as shown by the flow arrow in FIG. 1. It will be appreciated that the tube 12 restricts the flow to a generally axial direction. The tube 12 is manufactured of a rigid material like ceramic, preferably alumina. The tube should have reasonably good heat conductivity and sufficient strength and rigidity to prevent external forces from acting on the pyroelectric detector 14. Pyroelectric materials also generally exhibit piezoelectric properties. Thus, if external forces are allowed to act on the pyroelectric detector, undesirable stray voltages can be produced that could mask or otherwise interfere with the output voltage signal based on temperature changes.

Figure 2:
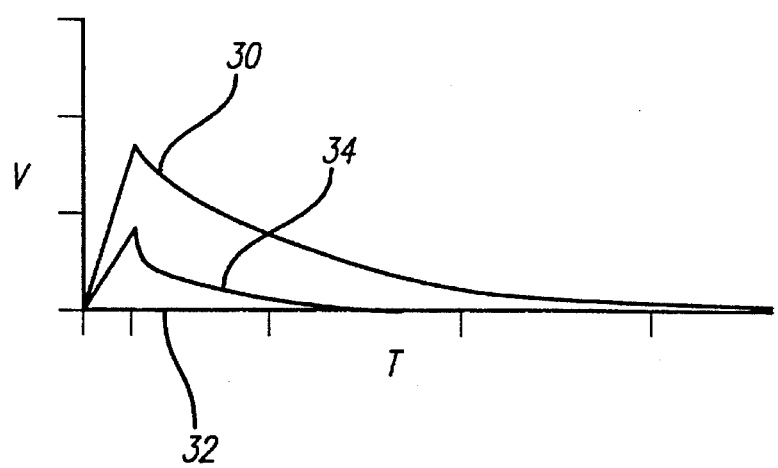
FIG. 2 is a graph of the time-varying output voltage signals associated with the flow sensor of FIG. 1.

Representative output voltage signals from the flow sensor 10 are shown in the graph of FIG. 2. The upper curve 30 indicates the output voltage signal with no fluid flow. The relatively steep inclined portion indicates the heating time period 32 during which the switch SW1 is closed and a predetermined amount of heat energy is provided by the heater 16. After the switch has been opened, the output voltage signal decays to zero at a rate based on the fluid flow. The lower curve 34 indicates a relatively high fluid flow rate. The inclined portion occurring during the heating time period is not as steep as it is during a non-flow condition, because the fluid is already removing heat from the sensor. After the heater has been switched off, the output voltage signal decays more rapidly in response to higher flow rate than it does in response to a lower flow rate. Accordingly, integrating the area under the curve of the decaying output voltage signal provides an indication of the flow rate. Likewise, sampling the output voltage signal after a predetermined time delay also provides an indication of the flow rate.

Figure 3:
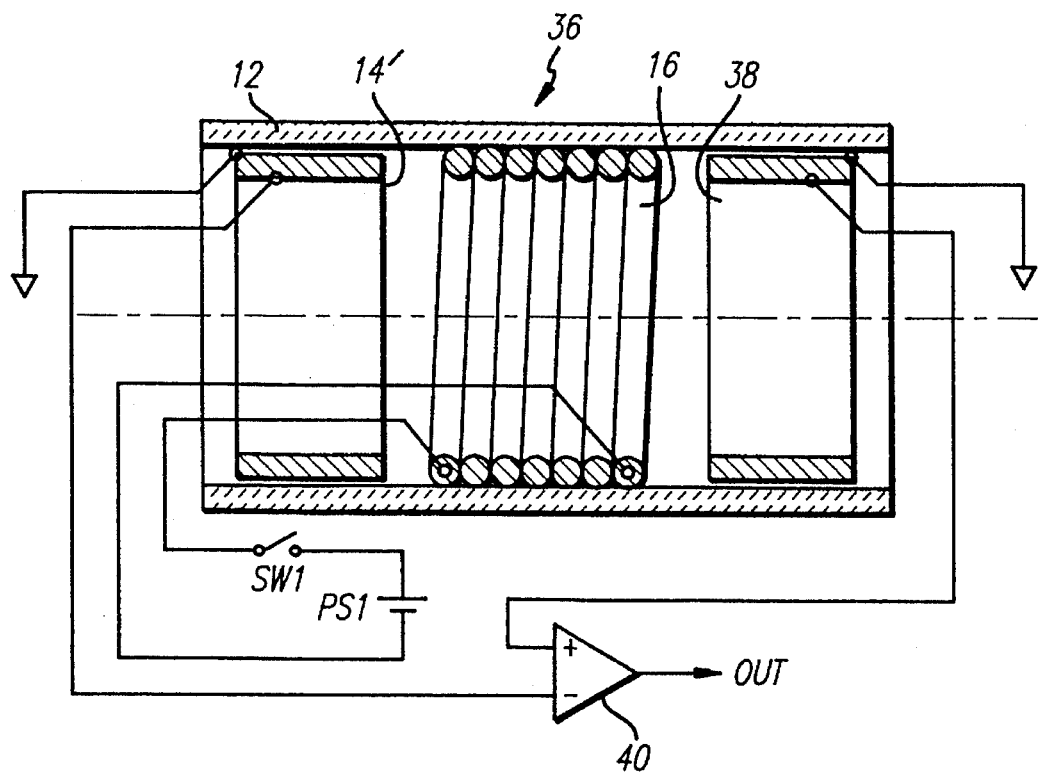
FIG. 3 is a cross-sectional view of a second embodiment of an implantable flow sensor of the present invention, which can indicate the direction of a fluid flow, with a schematic depiction of its associated control and monitoring circuitry.

A second embodiment of an implantable flow sensor 36, which also detects the direction of the fluid flow, is shown in FIG. 3. Having information regarding the direction of fluid flow is important in a situation where a heart valve may be leaky, allowing a back flow through the valve. The flow sensor 10 (FIG. 1) can improperly consider a back flow as a positive flow instead of a negative flow, thereby compounding the error in the flow rate indication. The FIG. 3 embodiment also is less sensitive to cross-flows; cross-flows will tend to change the flow sensor's sensitivity, but not appear as a true axial flow.

The flow sensor 36 is constructed and operates in a manner similar to the flow sensor 10 shown in FIG. 1. However, the flow sensor includes a second pyroelectric detector 38 identical to the first pyroelectric detector 14', but at the opposite end of the tube 12, with the heater 16 located between the two detectors. The output voltage signal of the first and second pyroelectric detectors 14 and 16 are supplied to a differential amplifier 40. The polarity of the signal from the differential amplifier indicates the direction of fluid flow. The differential amplifier 40 can be eliminated by reversing the polarity of one of the pyroelectric detectors 14' and 38 or by reconnecting the pyroelectric detectors as a series bucking pair, or in parallel.

Flow direction is determined on the basis of temperature differential between the upstream sensor, which will have a lower temperature and the downstream sensor, which will have a higher temperature, relative to each other.

Figure 4:
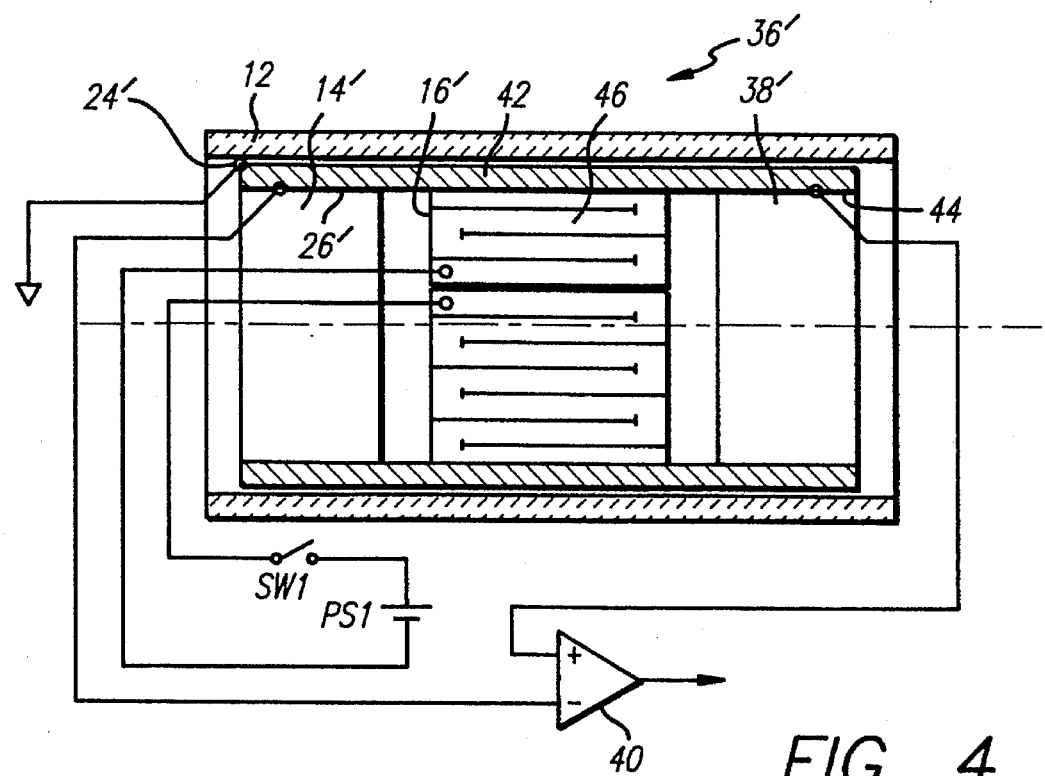
FIG. 4 is a cross-sectional view of a third embodiment of an implantable flow sensor of the present invention, which can indicate the direction of fluid flow, with a schematic depiction of its associated control and monitoring circuitry.

In a similar embodiment, depicted in FIG. 4, an implantable flow sensor 36' also detects the direction of fluid flow. However, in this embodiment, the two pyroelectric detectors 14' and 38' and the heater 16' are integrated into one long cylinder 42 of pyroelectric material. The outside of the cylinder consists of one large grounded electrode 24'. The inside of the cylinder has three electrodes, 26' 44, and 46.

The first and second electrodes 26' and 44 are similar to the electrode 26 of FIG. 1. The third electrode 46 forms the heater 16'. Preferably, the third electrode forms a serpentine path on the inside surface of the cylinder. Otherwise, the flow sensor 36' operates in a similar manner to the flow sensor 36 of FIG. 3.

A fourth embodiment of an implantable flow sensor 48 in accordance with the present invention is shown in FIG. 5. In this embodiment, a cylindrical pyroelectric detector 50 extends nearly the entire length of the tube 52. The heater 54 extends nearly the whole length of the detector cylinder. In this embodiment, the heat flows radially and the tube may be of a heat conductive material, such as a metal or diamond. This flow sensor does not detect the direction of the fluid flow.

A similar embodiment of a radially-acting flow sensor 48' is shown in FIG. 6. In this embodiment, the heater 54' is a serpentine path formed directly in the interior electrode 56 of the cylindrical pyroelectric detector 50'. Since the interior electrode 56 serves both as the heater and as one of the electrodes for the pyroelectric detector, the connection to the interior electrode must be multiplexed between the power source PS1 and the amplifier 28 by a suitable double-pole, double-throw switch 58 or the like.

Figure 7:
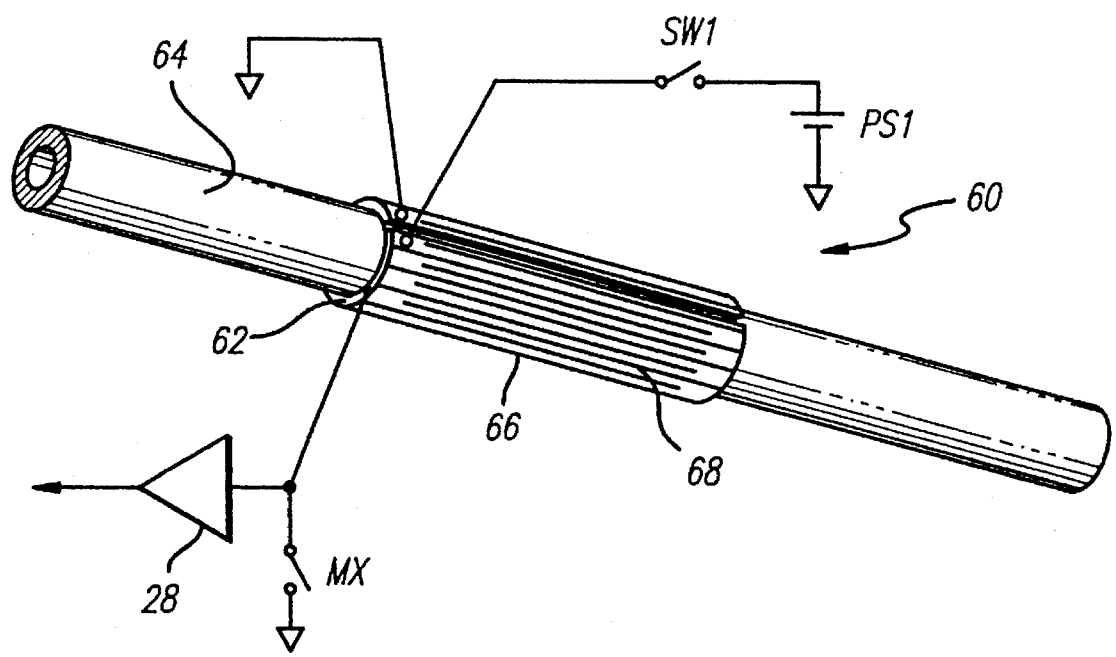
FIG. 7 is a perspective view of a sixth embodiment of the implantable flow sensor of the present invention having an integral heater element mounted on the outside of a tube, with a schematic depiction of control and monitoring circuitry for reducing stray signals induced during normal operation.
Figure 8:
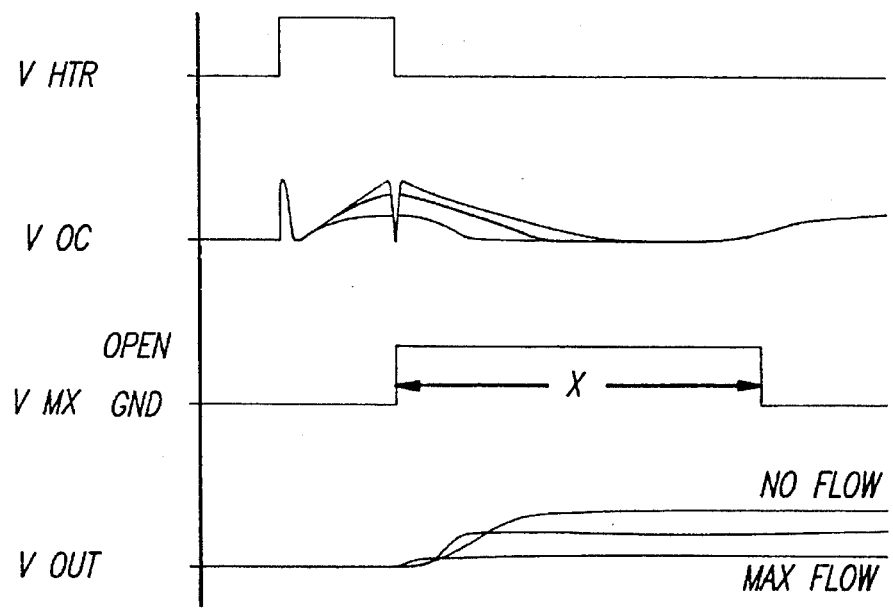
FIG. 8 is a graph that shows the control and the output voltage signals associated with the flow sensor of FIG. 7.
Figure 9:
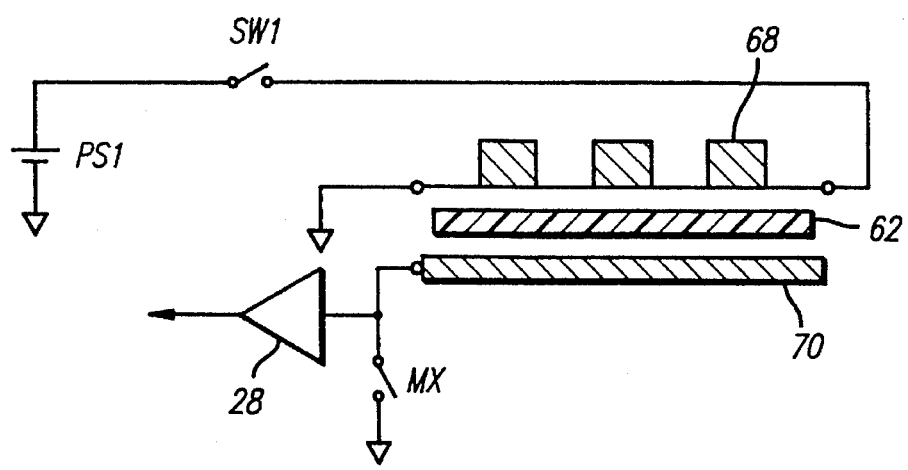
FIG. 9 is a schematic diagram of a circuit for eliminating induced noise on the output signal of the flow sensor of FIG. 7.

A sixth embodiment of a flow sensor 60 of the present invention is shown in FIGS. 7–9. This embodiment includes a cylindrical pyroelectric detector 62 in the form of a cylinder that encircles a tube 64, and further includes a heater 66 in the form of a serpentine electrode 68 on the outside surface of the detector cylinder. One end of the serpentine electrode is connected directly to electrical ground and the other end is connected to the power supply PS1 through the switch SW1. An interior electrode 70 (FIG. 9) is connected to the amplifier 28. In practice, there would be an electrical insulating layer (not shown) covering serpentine electrode 68 to prevent electrical communication between such electrode and the blood.

The voltage signals (FIG. 8) indicate that when the heater 66 is turned on and off, as indicated by the heater voltage signal Vhtr, voltage spikes would occur in the open-circuit output voltage signal Voc. To eliminate the voltage spikes, a second switch MX is placed between the interior electrode 70 and electrical ground. The switch MX remains closed, as indicated by switch voltage signal Vmx, shorting the output of the pyroelectric device until the end of the heater pulse. The switch MX then opens for a time period X, allowing the amplifier 28 to receive and buffer the output voltage signal and to produce a flow voltage signal, Vout. The larger the flow rate, the lower the amplitude of the flow voltage signal. Switch MX also serves to "zero" the amplifier output to facilitate differential measurements.

This feature of having a switch MX for eliminating induced voltage spikes on the output voltage signal is useful in small compact devices, especially those using a serpentine heater element that also acts as the detector, which are more susceptible to have problems with induced voltage signals.

It will be appreciated that a charge amplifier, known in the art, may be utilized in place of the voltage amplifier just described. Accordingly, a shorting switch (such as MX of FIG. 7) would be coupled to the input terminal of the amplifier, as well as to the output terminal of the amplifier, to prevent stray signals and to "zero" the amplifier output to facilitate differential measurements.

Although the foregoing discloses preferred embodiments of the present invention, it is understood that those skilled in the art may make various changes to the preferred embodiment shown without departing from the scope of the invention. The invention is defined only by the following claims.

What is claimed is:

1. An implantable flow sensor for measuring a rate of fluid flow within a fluid path, comprising:

a rigid tube sized to fit within the fluid path and to allow the fluid to flow along the tube;

a heater located within the tube and adapted to produce a predetermined amount of heat energy to increase the temperature of fluid within the fluid path;

a first pyroelectric detector adapted to detect changes in temperature caused by the heat energy and to generate a temperature signal based on the temperature change, wherein the first pyroelectric detector is coaxially located within the tube such that external forces applied to the tube are not transferred to the first pyroelectric detector; and a processor that generates a data signal, based on the temperature signal, that indicates the fluid flow rate within the fluid path.

2. An implantable flow sensor, as defined in claim 1, wherein the heater is a resistance heating element.

3. An implantable flow sensor, as defined in claim 2, wherein:

the first pyroelectric detector includes first and second electrodes spaced apart from each other by a pyroelectric material, and the first electrode is configured to serve as the resistive heating element.

4. An implantable flow sensor, as defined in claim 3, wherein the first electrode is etched in a serpentine path on one surface of the pyroelectric detector, to form the resistive heating element.

5. An implantable flow sensor, as defined in claim 1, wherein:

the rigid tube has a cylindrical shape.

6. An implantable flow sensor, as defined in claim 1, further comprising a second pyroelectric detector that operates in conjunction with the first pyroelectric detector to measure the direction of fluid flow.

7. An implantable flow sensor for measuring a rate of fluid flow within a fluid path, comprising:

a rigid tube sized to fit within the fluid path to allow the fluid to flow along the tube;

a pyroelectric detector, formed of a relatively thin sheet of pyroelectric material coaxially located within the tube and attached to an inside surface of the tube such that external forces applied to the tube are not transferred to the pyroelectric detector, wherein the pyroelectric detector detects changes in temperature and generates a temperature signal based on the temperature change, the pyroelectric detector having a first detector electrode sandwiched between the tube surface and one surface of the pyroelectric material and having a second detector electrode that is etched in a serpentine path on the other surface of the pyroelectric detector to form a heater;

an electrical power source that is switchably connected to the heater for a predetermined time period to cause the heater to produce a predetermined amount of heat energy;

an amplifier having an input terminal that receives the temperature signal from the pyroelectric detector allowing the amplifier to buffer the received temperature signal and produce a data signal that indicates the fluid flow rate within the fluid path; and a switch connected to the input terminal of the amplifier and configured to operate during the predetermined time period so that stray signals produced by currents through the heater are not received by the amplifier.

8. A blood flow sensor for measuring a flow rate of blood pumped by a person's heart through a blood vessel and for supplying a data signal indicating the measured blood flow rate to an implantable heart pacemaker, comprising:

a rigid cylindrical tube sized to fit within the blood vessel and to allow the blood to flow along the tube;

a heater located within the tube and adapted to produce a predetermined amount of heat energy to increase the temperature of blood within the blood vessel;

a first pyroelectric detector coaxially located within the tube and adapted to detect changes in temperature caused by the heat energy and to generate a temperature signal based on the temperature change; and a processor that generates the data signal, based on the temperature signal, that indicates the blood flow rate through the blood vessel.

9. A method for measuring a rate of fluid flow within a fluid path, comprising:

providing a rigid tube sized to fit within the fluid path and to allow the fluid to flow along the tube;

heating the fluid and tube by supplying a predetermined quantity of heat energy; and providing a first pyroelectric detector coaxially located within the tube that detects changes in temperature caused by the heating and generates a temperature signal based on the temperature change, wherein external forces applied to the tube are not transferred to the first pyroelectric detector; and processing the temperature signal to generate a data signal that indicates the fluid flow rate within the fluid path.

10. A method for measuring a rate of fluid flow within a fluid path as defined in claim 9, wherein:

the step of providing a first pyroelectric detector comprises providing first and second electrodes spaced apart from each other by a pyroelectric material; and the step of the heating the fluid and tube comprises using the first electrode to heat the fluid and tube.

11. A method for measuring a rate of fluid flow within a fluid path, as defined in claim 9, wherein the first electrode is etched in a serpentine path on the surface of the pyroelectric detector to form the resistive heating element.

12. A method for measuring a rate of fluid flow within a fluid path, as defined in claim 9, further comprising, providing a second pyroelectric detector that operates in conjunction with the first pyroelectric detector to measure the direction of fluid flow.

13. An implantable flow sensor for measuring a rate of fluid flow within a fluid path, comprising:

a rigid tube sized to fit within the fluid path and to allow fluid to flow along the tube;

a heater adapted to increase the temperature of fluid within the fluid path; and a pyroelectric detector coaxially located within the tube such that external forces applied to the tube are not transferred to the pyroelectric detector, the pyroelectric detector adapted to detect changes in temperature and to generate a temperature signal based on the temperature change.

14. An implantable flow sensor for measuring a rate of fluid flow within a fluid path, comprising:

a rigid tube sized to fit within the fluid path to allow fluid flow a fluid path; and a pyroelectric detector, formed of a relatively thin sheet of pyroelectric material attached to a surface of the tube, wherein the pyroelectric detector detects changes in temperature and generates a temperature signal based on the temperature change, the pyroelectric detector having a first detector electrode sandwiched between the tube surface and one surface of the pyroelectric material and having a second detector electrode that is etched in a serpentine path on the other surface of the pyroelectric detector to form a heater, wherein the pyroelectric detector is coaxially located within the tube such that external forces applied to the tube are not transferred to the pyroelectric detector.

* * * * *